United States Patent [19]

Miller

[11] Patent Number: 5,312,991

[45] Date of Patent: May 17, 1994

[54] SURFACTANT IMPROVEMENT FOR PARA-AMINOPHENOL PROCESS

[75] Inventor: Douglas C. Miller, St. Louis, Mo.

[73] Assignee: Mallinckrodt Specialty Chemicals Company, Chesterfield, Mo.

[21] Appl. No.: 895,632

[22] Filed: Jun. 9, 1992

[51] Int. Cl.$^5$ ............................................. C07C 213/00
[52] U.S. Cl. ................................................... 564/418
[58] Field of Search ........................................ 564/418

[56] References Cited

U.S. PATENT DOCUMENTS

| | | | |
|---|---|---|---|
| 2,198,249 | 4/1940 | Henke et al. | 260/509 |
| 2,765,342 | 10/1956 | Spiegler | 260/575 |
| 3,383,416 | 5/1968 | Benner | 260/575 |
| 3,535,382 | 10/1970 | Brown et al. | 260/575 |
| 4,176,138 | 11/1979 | Sathe | 260/575 |
| 4,307,249 | 12/1981 | Derrenbacker | 546/418 |
| 4,885,389 | 12/1989 | Lee et al. | 564/418 |

Primary Examiner—Richard L. Raymond
Assistant Examiner—Brian M. Burn
Attorney, Agent, or Firm—Rothwell, Figg, Ernst & Kurz

[57] ABSTRACT

The compound p-aminophenol is prepared by catalytically hydrogenating nitrobenzene in an acidic reaction medium containing an amine of the formula (I)

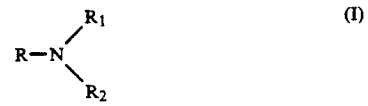

wherein R represents an alkyl group having from 6 to about 20 carbon atoms; $R_1$ and $R_2$ are the same or different, and are represented by the formula $-[(CH_2)_mO]_nH$, wherein m is an integer of from 1 to about 5 and n is an integer of from 1 to about 10.

20 Claims, No Drawings

SURFACTANT IMPROVEMENT FOR PARA-AMINOPHENOL PROCESS

BACKGROUND OF THE INVENTION

1. Field of the Invention

The present invention relates to improvements in a process for the preparation of p-aminophenol from nitrobenzene.

2. Description of the Background Art

The compound p-aminophenol (PAP) is an important chemical intermediate used in the preparation of the analgesic acetaminophen. A number of other derivatives having a wide variety of industrial applications may also be prepared from PAP. One method for preparing PAP involves the catalytic hydrogenation of nitrobenzene in an acid medium. In this process, phenylhydroxylamine is first formed, and this intermediate promptly rearranges in the acid reaction medium to form PAP.

Henke, et al. (U.S. Pat. No. 2,198,249) reportedly were the first to disclose a process for the preparation of PAP by the catalytic hydrogenation of nitrobenzene in an acid medium.

A number of process variations have since been disclosed. For example, Spiegler (U.S. Pat. No. 2,765,342) studied the reaction extensively. Among the factors explored by Spiegler was the effect on reduction rate and p-aminophenol yield of including a surfactant selected from among quaternary ammonium compounds and several non-quaternary compounds. Among the quaternary ammonium compounds used was dodecyl trimethylammonium chloride. The non-quaternary compounds investigated include two simple tertiary amine salts: triethylamine sulfate and tributylamine sulfate, as well as dioctadecyl propyleneamine dioleate. From a plot of rate and yield data, Spiegler concluded that the rate/yield performance of all of the quaternary ammonium compounds examined was superior to that of the non-quaternary compounds.

Later, Brown et al. (U.S. Pat. No. 3,535,382) reported that certain nonionic polyether polyol surfactants could be substituted for Spiegler's quaternary ammonium compounds.

R.G. Benner (U.S. Pat. No. 3,383,416) used the Henke et al. approach of charging all the nitrobenzene at once, but used a carbon-supported platinum catalyst and quaternary ammonium surfactant, preferably dodecyl trimethylammonium chloride, as disclosed by Spiegler. Benner purposely interrupted the hydrogenation well before all the nitrobenzene had been consumed. In the presence of two liquid phases, aqueous and nitrobenzene, a carbon-supported platinum catalyst is preferentially wetted by the nitrobenzene, so most of the catalyst is suspended in the nitrobenzene layer, permitting the removal of the upper aqueous solution of PAP and aniline by decantation. The PAP is then recovered from the aqueous layer and purified.

While Benner proposed quaternary ammonium salts as the surfactant, other surfactants have been utilized, including amine oxide (Sathe, U.S. Pat. No. 4,176,138) and amine salts (Derrenbacher, U.S. Pat. No. 4,307,249). Use of these surfactants tends to result in formation of stable emulsions, which makes separation of the desired PAP product difficult.

There remains a need in the art for improvements in the process for preparing p-aminophenol by catalytic hydrogenation of nitrobenzene.

SUMMARY OF THE INVENTION

In accordance with the present invention, a process for preparing p-aminophenol comprises catalytically hydrogenating nitrobenzene in an acidic reaction medium containing an alkoxylated fatty amine of the formula (I):

wherein R represents alkyl having from about 6 to about 20 carbon atoms; $R_1$ and $R_2$ are the same or different, and are represented by the formula $-[(CH_2)_mO]_nH$, wherein m is an integer of from 1 to about 5, and n is an integer from 1 to about 10.

DETAILED DESCRIPTION OF THE PREFERRED EMBODIMENTS

The improved process of the present invention involves catalytic hydrogenation of nitrobenzene in an acid reaction medium containing an alkoxylated fatty amine surfactant of the formula (I) as set forth above, wherein R, $R_1$ and $R_2$ are as previously defined. In preferred embodiments, the acidifying agent is sulfuric acid, although other acids can be used.

In preferred embodiments of the present invention, the alkyl group R has from about 8 to about 16 carbon atoms, more preferably from about 10 to about 14 carbon atoms, and most preferably 12 carbon atoms. The alkyl group R can be branched, but in preferred embodiments is straight chain.

As noted above, $R_1$ and $R_2$ can be the same or different, and are represented by the formula $-[(CH_2)_mO]_nH$, wherein m is an integer of from 1 to about 5, and n is an integer from 1 to about 10. In preferred embodiments, m is 2 or 3, most preferably 2.

In accordance with one aspect of the embodiment wherein $R_1$ and $R_2$ are the same and m is 2, n is preferably 1. In a particularly preferred embodiment wherein n is 1 for both $R_1$ and $R_2$, R is a straight chain alkyl group having about 12 carbon atoms.

In another embodiment, $R_1$ and $R_2$ are different. In accordance with one aspect of this embodiment, m is 2 and n is 2 or 3. In a preferred aspect of this embodiment wherein m is 2 and $R_1$ and $R_2$ are different, R is a straight chain alkyl group of about 12 carbon atoms. In accordance with a particularly preferred aspect of this embodiment, the n of $R_1$ is 2 and the n of $R_2$ is 3.

In yet another embodiment wherein $R_1$ and $R_2$ are different, m preferably is 2, and the n of $R_1$ is 8 while the n of $R_2$ is 7.

During catalytic hydrogenation of nitrobenzene in the acid reaction medium, the amine surfactant of the present invention can be present in the reaction medium at a concentration within the range of from about 0.1–50 g/l, preferably about 0.5–25 g/l, and more preferably about 1–15 g/l.

The invention is illustrated by the following examples, which are not intended to be limiting.

EXAMPLE I

The following reagents were charged into a six liter glass hydrogenator equipped with Teflon coated mechanical agitator and Teflon coated baffles: 4000 ml deionized water, 1200 g nitrobenzene, 2 g 1.5% platinum on carbon catalyst, 4 g Ethomeen TM C/12 (Akzo Inc.) surfactant, and 665 g sulfuric acid. The mixture was heated to 80 degrees C under a nitrogen atmosphere. The reactor then was purged with hydrogen, pressurized to 10 psig, and the agitation increased to 1000 rpm. After 2.5–3.0 hours the agitation was stopped and the reactor purged with nitrogen. After cooling to room temperature the two phases were separated and the aqueous phase analyzed by HPLC. The results were compared in the following Examples to a standard experiment with docezyldimethyl amine (ADMA TM 2, Ethyl Corp.) as the surfactant.

EXAMPLE II

Emulsions were prepared by adding an acidic solution of p-aminophenol and surfactant (50 g PAP/l, 15% sulfuric acid, and 2 g surfactant/l) to a rapidly stirred mixture of nitrobenzene and carbon. The resulting emulsions were transferred to graduated cylinders and placed in a water bath at 75 degrees C. The time required for the phases to separate was recorded and taken as a measure of emulsion stability.

The results are shown in Table 1 below:

TABLE 1

| Time | Emulsion Volume, ml | | |
|---|---|---|---|
| | ADMA TM 2 | Ethomeen TM C/12 | Ethomeen TM C/15 |
| 0:30 | 50 | 20 | 40 |
| 1:00 | 50 | | 35 |
| 1:30 | | 15 | |
| 2:00 | 45 | | 30 |
| 2:30 | | 12 | |
| 5:00 | 25 | | 20 |

Specifications for Table 1: 50 mg/ml PAP, 2.0 mg/ml Surfactant, 14.5 w/v Sulfuric Acid, 5.0 mg/ml carbon, 0.25 O/A (organic to aqueous ratio by volume).

EXAMPLE III

Emulsions were prepared and tested as in Example II, except with the specifications set forth below. The results are shown in Table 2 below:

TABLE 2

| Time | Emulsion Volume, ml | | |
|---|---|---|---|
| | ADMA TM 2 | Ethomeen TM C/12 | Ethomeen TM C/15 |
| 0:30 | 50 | 7 | 50 |
| 1:00 | 50 | 10 | 50 |
| 1:30 | 50 | 10 | 50 |
| 2:00 | 50 | 10 | 50 |
| 2:30 | 50 | 10 | 50 |

Specifications for Table 2: 50 mg/ml PAP, 12.0 mg/ml Surfactant, 14.5 w/v Sulfuric Acid, 5.0 mg/ml carbon, 0.25 O/A.

EXAMPLE IV

Emulsions were prepared and tested as in Example II, except with the specifications set forth below. The results are shown in Table 3.

TABLE 3

| Time | Emulsion Volume, ml | | |
|---|---|---|---|
| | ADMA TM 2 | Ethomeen TM C/12 | Ethomeen TM C/15 |
| 0:30 | 50 | 15 | 50 |
| 1:00 | 50 | 13 | 40 |
| 1:30 | 50 | 11 | 25 |
| 2:00 | 50 | 11 | 25 |
| 2:30 | 50 | 11 | 25 |
| 3:00 | 50 | 11 | 20 |

Specifications for Table 3 50 mg/ml PAP, 1.0 mg/ml Surfactant, 14.5 w/v Sulfuric Acid 5.0 mg/ml carbon, 0.25 O/A.

EXAMPLE V

Surfactants Ethomeen TM C/12 and Ethomeen TM C/15 were tested in a six liter hydrogenator and compared to ADMA TM 2. Both equivalent weight and moles of the two Ethomeen TM products were used. The results are summarized in Table 4 below.

TABLE 4

| Surfactant | Weight, g | mg-moles | Rate (gPAP/hr) | Yield (%) | [PAP]/[Anl] |
|---|---|---|---|---|---|
| ADMA TM 2 | 3.12 | 15 | 228.8 | 72.68 | 5.11 |
| Ethomeen TM C/12 | 4.18 | 15 | 213.7 | 75.89 | 6.63 |
| Ethomeen TM C/15 | 6.18 | 15 | 214.8 | 73.84 | 5.55 |
| Ethomeen TM C/12 | 3.12 | 11 | 206.1 | 73.03 | 6.03 |
| Ethomeen TM C/15 | 3.12 | 7 | 204.5 | 74.97 | 4.81 |

On an equivalent mole basis, both of the Ethomeen TM products settled faster than ADMA TM. Both of the Ethomeen TM products exhibited higher yield and selectivity, although the Ethomeen TM C/12 product was better yet. For equivalent weight charges, the rates for both Ethomeen TM products were about the same, but slightly lower than the equivalent mole basis experiments. The yield and selectivity were also lower, but Ethomeen TM C/12 was still better than ADMA TM.

In all cases, the Ethomeen TM C/12 product exhibited the greatest emulsion instability. The emulsions were considerably less stable than with ADMA TM, and also less stable than Ethomeen TM C/15. A reduction in emulsion stability is very beneficial for commercial production of PAP, since a considerable amount of down time associated with commercial production of PAP is due to emulsion related problems.

Furthermore, in a recycle experiment, use of Ethomeen TM C/12 was found to result in much greater catalyst recycle activity than use of ADMA, which may allow reduced catalyst use. Additionally, solid PAP which was isolated from the recycle experiment with Ethomeen TM C/12, was compared to PAP isolated from a typical experiment with ADMA. No unusual impurities were found in the HPLC assay of the PAP from the Ethomeen TM C/12 recycle experiment.

I claim:

1. A process for preparing p-aminophenol comprising catalytically hydrogenating nitrobenzene in an acidic reaction medium containing an amine of the formula (I)

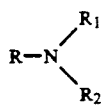
(I)

wherein R represents alkyl having from about 6 to about 20 carbon atoms; R and $R_2$ are the same or different, and are represented by the formula —[(CH$_2$)$_m$O]$_n$H, wherein m is an integer of from 1 to about 5 and n is an integer of from 1 to about 10.

2. The process of claim 1 wherein said alkyl group has from about 8 to about 16 carbon atoms.

3. The process of claim 1 wherein said alkyl group has from about 10 to about 14 carbon atoms.

4. The process of claim 1 wherein said alkyl group has about 12 carbon atoms.

5. The process of claim 4 wherein R is a branched alkyl group.

6. The process of claim 1 wherein m is 2 or 3.

7. The process of claim 1 wherein m is 2.

8. The process of claim 7 wherein said alkyl group has about 12 carbon atoms.

9. The process of claim 8 wherein R is a straight chain alkyl group.

10. The process of claim 9 wherein $R_1$ and $R_2$ are the same.

11. The process of claim 10 wherein n of both $R_1$ and $R_2$ is 1.

12. The process of claim 11 wherein said reaction medium contains said amine at a concentration within the range of about 0.1–15 g/l.

13. The process of claim 11 wherein said reaction medium contains said amine at a concentration within the range of about 0.5–25 g/l.

14. The process of claim 11 wherein said reaction medium contains said amine at a concentration of about 1–15 g/l.

15. The process of claim 9 wherein $R_1$ and $R_2$ are different.

16. The process of claim 15 wherein n is 2 or 3.

17. The process of claim 16 wherein in $R_1$, n is 2; and in $R_2$, n is 3.

18. The process of claim 17 wherein said reaction medium contains said amine at a concentration within the range of about 0.1–50 g/l.

19. The process of claim 17 wherein said reaction medium contains said amine at a concentration within the range of about 0.5–25 g/l.

20. The process of claim 17 wherein said reaction medium contains said amine at a concentration of about 1–15 g/l.

* * * * *

UNITED STATES PATENT AND TRADEMARK OFFICE
CERTIFICATE OF CORRECTION

PATENT NO. : 5,312,991
DATED : May 17, 1994
INVENTOR(S) : Douglas C. Miller

It is certified that error appears in the above-indentified patent and that said Letters Patent is hereby corrected as shown below:

Col. 5, line 9, "R" should be --$R_1$--.

Signed and Sealed this

Sixteenth Day of August, 1994

Attest:

BRUCE LEHMAN

Attesting Officer

Commissioner of Patents and Trademarks